US007452713B2

(12) United States Patent
Barlocchi et al.

(10) Patent No.: US 7,452,713 B2
(45) Date of Patent: Nov. 18, 2008

(54) PROCESS FOR MANUFACTURING A MICROFLUIDIC DEVICE WITH BURIED CHANNELS

(75) Inventors: Gabriele Barlocchi, Cornaredo (IT); Pietro Corona, Milan (IT); Ubaldo Mastromatteo, Bareggio (IT); Flavio Villa, Milan (IT)

(73) Assignee: STMicroelectronics S.r.l., Agrate Brianza (IT)

( * ) Notice: Subject to any disclaimer, the term of this patent is extended or adjusted under 35 U.S.C. 154(b) by 442 days.

(21) Appl. No.: 11/191,325

(22) Filed: Jul. 28, 2005

(65) Prior Publication Data

US 2005/0282221 A1 Dec. 22, 2005

Related U.S. Application Data

(60) Continuation-in-part of application No. 10/712,211, filed on Nov. 12, 2003, now Pat. No. 6,992,367, which is a division of application No. 09/797,206, filed on Feb. 27, 2001, now Pat. No. 6,693,039.

(30) Foreign Application Priority Data

Feb. 29, 2000 (EP) .................................. 00830148

(51) Int. Cl.
*C12M 1/34* (2006.01)
*C12M 3/00* (2006.01)

(52) U.S. Cl. ....................... 435/288.5; 435/6; 435/91.2; 435/287.2; 435/303.1

(58) Field of Classification Search .............. 435/288.5, 435/287.1, 6, 91.2, 287.2, 303.1
See application file for complete search history.

(56) References Cited

U.S. PATENT DOCUMENTS 5,429,734 A 7/1995 Gajar et al.
5,637,469 A 6/1997 Wilding et al.
5,639,423 A 6/1997 Northrup et al.
5,856,174 A * 1/1999 Lipshutz et al. .......... 435/286.5
5,922,591 A 7/1999 Anderson et al.
5,939,312 A 8/1999 Baier et al.
5,942,443 A 8/1999 Parce et al.
6,046,056 A 4/2000 Parce et al.
6,168,948 B1 1/2001 Anderson et al.
6,174,675 B1 * 1/2001 Chow et al. .................... 435/6
6,261,431 B1 7/2001 Mathies et al.

(Continued)

FOREIGN PATENT DOCUMENTS

EP 1043770 A1 10/2000

(Continued)

OTHER PUBLICATIONS

Esashi et al. Vacuum-Sealed Silicon Micromachined Pressure Sensors. 1998. Proceedings of the IEEE, vol. 86, No. 8, p. 1627-1639.*

*Primary Examiner*—Walter D. Griffin
*Assistant Examiner*—Shanta G Doe
(74) *Attorney, Agent, or Firm*—Baker & McKenzie LLP

(57) ABSTRACT

A process for manufacturing a microfluidic device, including the steps of: forming at least one channel in a semiconductor material body; forming a dielectric diaphragm above the channel, for closing the channel; and forming heating elements for providing thermal energy inside the channel. The heating elements are formed directly on said dielectric diaphragm.

18 Claims, 6 Drawing Sheets

U.S. PATENT DOCUMENTS

| | | | |
|---|---|---|---|
| 6,267,858 | B1 | 7/2001 | Parce et al. |
| 6,326,083 | B1 * | 12/2001 | Yang et al. .................. 428/429 |
| 2001/0036672 | A1 | 11/2001 | Anderson et al. |
| 2002/0022261 | A1 | 2/2002 | Anderson et al. |
| 2002/0045244 | A1 | 4/2002 | Barlocchi et al. |
| 2002/0055167 | A1 | 5/2002 | Pourahmadi et al. |
| 2002/0060156 | A1 | 5/2002 | Mathies et al. |
| 2002/0068334 | A1 | 6/2002 | Carrino et al. |
| 2002/0068357 | A1 | 6/2002 | Mathies et al. |
| 2003/0057199 | A1 | 3/2003 | Villa et al. |

FOREIGN PATENT DOCUMENTS

| | | | |
|---|---|---|---|
| EP | 1049157 | A1 | 11/2000 |
| EP | 1130631 | A1 | 5/2001 |
| EP | 1123739 | A1 | 8/2001 |

* cited by examiner

16"
51
18"
50
11"

10"
16"
52
54
63
62
61
65
58
60
56
64

66

PROCESS FOR MANUFACTURING A MICROFLUIDIC DEVICE WITH BURIED CHANNELS

PRIOR RELATED APPLICATIONS

This application is a continuation-in-part of U.S. Ser. No. 10/712,211 filed Nov. 12, 2003 and published Jun. 3, 2004 as US20040106290; which is a divisional of U.S. Ser. No. 09/797,206 filed Feb. 27, 2001 and issued Feb. 17, 2004 as U.S. Pat. No. 6,693,039; and claims the benefit of EP Application No. 00830148.3 filed Feb. 29, 2000 and issued Sep. 5, 2001 as EP1130631. Each application is incorporated by reference in its entirety.

FEDERALLY SPONSORED RESEARCH STATEMENT

Not applicable.

REFERENCE TO MICROFICHE APPENDIX

Not applicable.

FIELD OF THE INVENTION

The invention relates to a process for manufacturing a microfluidic device with buried channels, devices with buried channels, and uses thereof.

BACKGROUND OF THE INVENTION

In general, chemical microreactors are provided with a microfluidic circuit, including microchannels. In the most advanced microfluidic devices the microchannels are buried in a substrate and/or in an epitaxial layer of a semiconductor chip. Substances to be processed, which are dispersed in a fluid medium, are supplied to one or more inlet reservoirs of the microfluidic circuit and are moved there through. Chemical reactions take place along the microfluidic circuit.

As is known, microfluidic devices may be exploited in a number of applications, and are particularly suited to be used as chemical microreactors. Thanks to the design flexibility allowed by semiconductor micromachining techniques, devices have been made that are capable of carrying out individual processing steps or even an entire chemical process.

For example, microfluidic devices are widely employed in biochemical processes, such as nucleic acid analysis. Such microreactors may also be called "Labs-On-Chip." The discussion herein is simplified by focusing on nucleic acid analysis as an example of a biological molecule that can be analyzed using the various devices of the invention. However, the various devices may be used for any chemical or biological test, although typically molecule purification is substituted for amplification and detection methods vary according to the molecule being detected. For example, another common diagnostic involves the detection of a specific protein by binding to its antibody or by a specific enzymatic reaction. Lipids, carbohydrates, drugs and small molecules from biological fluids are processed in similar ways.

DNA amplification involves a series of enzyme-mediated reactions resulting in identical copies of the target nucleic acid. In particular, Polymerase Chain Reaction (PCR) is a cyclical process where the number of DNA molecules substantially doubles at every iteration, starting from a mixture comprising target DNA, enzymes (typically a DNA polymerase such as TAQ), primers, the four dNTPs, cofactor, and buffer.

During a cycle, double stranded DNA is first separated into single strands (denatured). Then the primers hybridize to their complementary sequences on either side of the target sequence. Finally, DNA polymerase extends each primer, by adding nucleotides that are complementary to the target strand. This doubles the DNA content and the cycle is repeated until sufficient DNA has been synthesized. RNA amplification is similar, but is typically preceded by copying the RNA into DNA.

Although PCR allows the production of millions of copies of the target sequence in few hours, in many cases its efficiency and speed might be improved by increasing the concentration of the reagents. Similarly, end-point detection of amplified DNA (amplicons) by hybridization is highly concentration dependant.

As already mentioned, in the most advanced microfluidic devices the channels are "buried" in a substrate and/or in an epitaxial layer of a semiconductor chip. However, processes for manufacturing microfluidic devices with buried channels are quite complicated. In particular, several steps are required once the buried channels have been completed and alignment of subsequent masks is often critical. Usually, additional steps are required to reveal the alignment signs of the wafer being processed, which would otherwise be hidden.

A known technique is described in "PROCEEDINGS OF THE IEEE," Vol. 86, No. 8, August 1998, page 1632, and essentially envisages the creation of a cavity or air gap by means of anisotropic chemical etches made using potassium hydroxide (KOH), tetramethyl ammonium hydroxide (TMAH), etc., and employing a sacrificial polycrystalline-silicon layer.

This technique is schematically illustrated in FIGS. 1a-1c, and essentially involves the deposition and definition, using a special mask, of a sacrificial polycrystalline-silicon layer 5 on the top surface of the substrate 1, deposition of a silicon-nitride (Si3N4) layer 6 above the sacrificial polycrystalline-silicon layer 5 (FIG. 1a), and then the carrying-out of an anisotropic etch of the substrate 1 through an opening 7 made in the silicon-nitride layer 6 (FIG. 1b). By means of the anisotropic etch, the sacrificial polycrystalline-silicon layer 5 and part of the substrate 1 are thus removed, and a cavity or air-gap 8 is obtained having a roughly triangular cross section, which is separated from the outside environment by a diaphragm 9 consisting of the portion of the silicon-nitride layer 6 overlying the cavity 8 (FIG. 1c), and on which the inductor can subsequently be made.

SUMMARY OF THE INVENTION

As used herein "buried channel" is defined as a channel or chamber that is buried inside of a single monolithic support, as opposed to a channel or chamber that is made by welding or otherwise bonding two supports with a channel or two half channels together.

According to one embodiment of the invention, a process for manufacturing a microfluidic device with buried channels is provided, as well as devices made by such process, and the various uses for such devices.

Generally speaking, true buried channels are made by anisotropically etching a substrate using a holed mask with apertures whose sides form an angle of 45°±1° with respect to the "flat" of the wafer. The apertures are arranged so that the longitudinal axes A of the buried channels are perpendicular to the flat of the wafer. Hence, each buried channel has a trapezoidal longitudinal section and a triangular cross section when etched to completion, or a trapezoidal cross section when etching is terminated short of completion.

Next, as a dielectric diaphragm is formed above each channel to close it, and heating elements are formed directly on said dielectric diaphragm. The dielectric diaphragm is made by depositing a coating film of a semiconductor material, partially occluding said apertures, thermally oxidizing said coating film, thereby narrowing said openings, and depositing a closing layer of a dielectric material, to completely close the openings.

The method thus avoids the use of epitaxial or pseudo-epitaxial layers and the need for a second mask, making it simpler and easier to fabricate a variety of devices.

BRIEF DESCRIPTION OF THE DRAWINGS

For a better understanding of the various embodiments of the invention, preferred embodiments thereof are now described, merely to provide non-limiting examples, with reference to the attached drawings, in which.

DESCRIPTION OF EMBODIMENTS OF THE INVENTION

Figure 2:
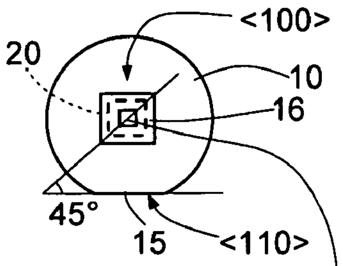
FIG. 2 shows a top view of a semiconductor wafer in which a cavity or air gap 20 is formed using a holed mask 16 having openings oriented at a selected angle with respect to a particular crystallographic plane of the wafer 10.
Figure 4:
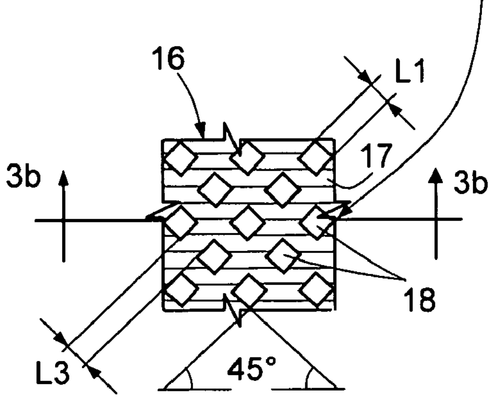
FIGS. 4 and 5 show portions of masks used during the process.

As is known, a crystal of a semiconductor wafer has a number of crystallographic planes, among them <110>, <100>, <111>. As shown in FIG. 2, some wafers have a flat 15 which has been previously formed along the crystallographic plane <110>. For those wafers having a flat 15, which is previously formed on the <110> plane, the side walls of the holes 18 are aligned at approximately 45° to this flat 15 (FIG. 4).

Alternatively, some semiconductor wafers do not contain the flat 15. Instead, they use other methods for identifying the crystallographic orientation of a plane. Thus, instead of using the flat of the wafer 15, some other method may be used to ensure that the orientation of the lattice structure is at the desired angle, relative to the selected plane.

Figure 3A:
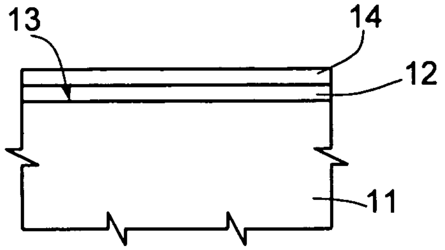
FIGS. 3*a*-3*d* show cross sections of the wafer of FIG. 2 at an enlarged scale in successive forming steps.

For forming the cavity 20, according to what is illustrated in FIGS. 3*a*-3*d*, directly on the top surface 13 of a P or P+ monocrystalline silicon substrate 11 (i.e., without the interposition of a sacrificial polycrystalline-silicon layer), a first silicon-dioxide layer 12 is initially grown having a thickness of between 200 Å and 600 Å, and a silicon-nitride layer 14 is next deposited thereon having a thickness of between 900 and 1500 Å (FIG. 3*a*).

Figure 3B:
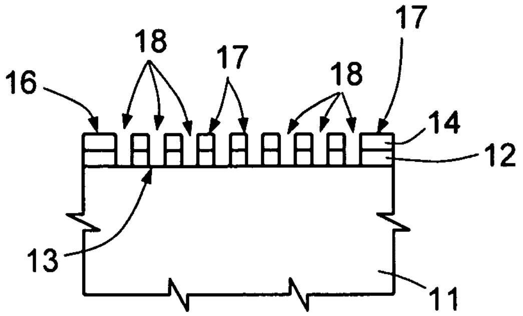

Next, using a resist mask (not shown), dry etching is carried out on the uncovered portions of the silicon-nitride layer 14 and the silicon-dioxide layer 12, and the resist mask is then removed. In this way, the portions of the silicon-nitride layer 14 and the silicon-dioxide layer 12 that have remained after the dry etching form the holed mask 16 as shown in FIG. 3*b* in cross-section and FIG. 4 in a top view.

As is illustrated in detail in FIG. 4, the holed mask 16 has a lattice structure with interstitial openings 18 having a substantially square cross section, with sides having a length L1 of, for example, between 1 μm and 3 μm, preferably 2 μm, and an inclination of 45°±1° with respect to the flat of the wafer 10, and thus, to the <110> plane. In some embodiments, the distance L3 is comparable to the length L1, and hence, for example, a distance of between 1 μm and 3 μm while in other embodiments, it may be larger or smaller. A region 17 between the apertures 18 forms distinct support columns delineating the apertures 18. Columns 17, interspersed with the apertures 18, form a lattice structure over the semiconductor surface as shown in FIG. 3*b* in preparation for etching.

Other mask configurations and angles may be used when the flat of the wafer, or other indicia, is not aligned with the <110>plane. For example, the angle may be between 30° to 60° for other orientations. In general, the angle range depends on the crystallographic orientation of the wafer relative to the mask.

Figure 3C:
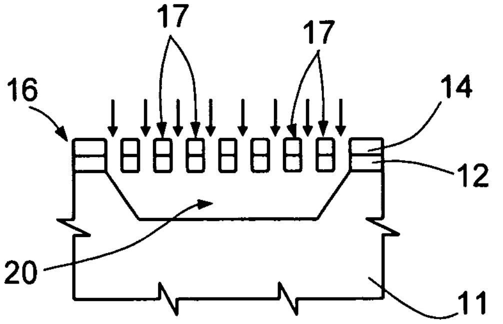
Figure 3D:
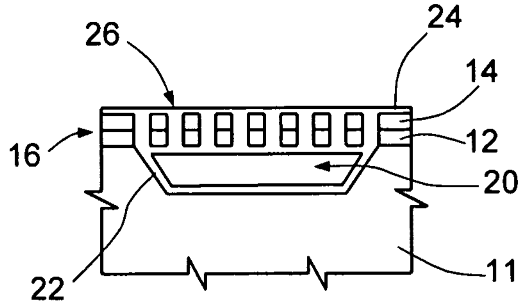

Using the holed mask 16, the substrate 11 is then anisotropically etched under time control in tetramethyl ammonium hydroxide (TMAH), thus forming the cavity 20, which substantially has the shape of an isosceles trapezium turned upside down and a uniform depth of between 50 μm and 100 μm (FIG. 3*c*).

In particular, the shape of an upside-down isosceles trapezium of the cavity 20 is obtained due to the combination of the following factors: execution of an anisotropic etch; use of a holed mask 16; and orientation at 45°±1° of the openings 18 with respect to the flat of the wafer 10. Also, length of etching time controls the bottom shape because a short etch time will lead to a flat bottom cavity, but if desired the etch can be continued until a triangle shaped cavity in cross section is achieved (see e.g., FIG. 9).

In fact, with the particular combination described above, the individual etches having their origin from the openings 18 of the holed mask 16 are performed on particular crystallographic planes of the silicon which enable the individual etches to "join up" laterally to one another, thus causing removal of the silicon not only in the vertical direction (i.e., in the direction of the depth of the substrate 11), but also in the horizontal direction (width/length), thus leading to the formation of the cavity 20 having the shape shown in FIG. 3*c*.

Figure 1A:
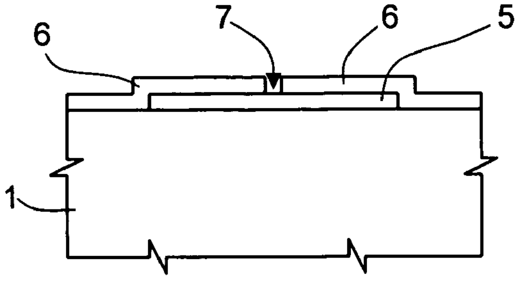
FIGS. 1*a*-1*c* show cross sections of a semiconductor material wafer in successive steps of a known forming process.
Figure 1B:
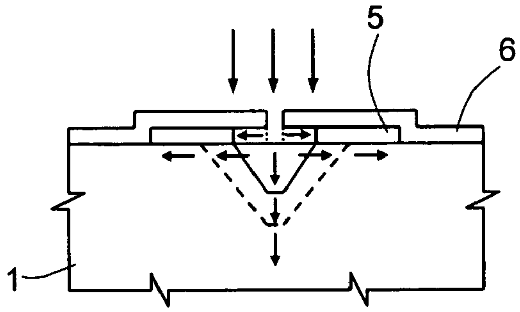
Figure 1C:
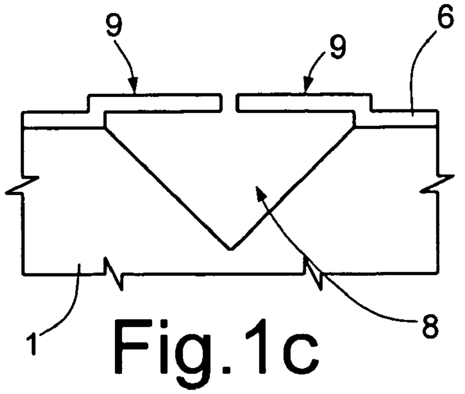

If, instead, the mask were oriented such that the openings 18 of the holed mask 16 had sides parallel or orthogonal to the flat of the wafer 10, the individual etches having their origin from the opening 18 of the holed mask 16 would be performed on crystallographic planes of the silicon that would not enable the individual etches to "join up" laterally to one another, thus leading to the formation of a set of cavities, equal in number to the openings 18 of the holed mask 16, separate from one another, and each having a cross section shaped like an upside-down triangle, of the same type as that shown in FIG. 1*c*.

Figure 5:
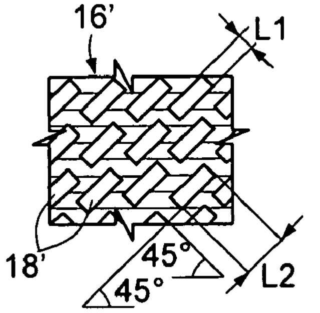

One factor in determining the configuration and the angle of orientation of the lattice structure is that as the etch progresses in the substrate underneath the lattice structure from one opening it must eventually meet up with another opening, as can be observed in FIGS. 4 and 5. The distance L3 is selected to permit proper etching while ensuring that the individual etches join up to form a single large cavity. Thus, in some instances, L3 could be large, compared to L1, while in other designs, it will approximately equal L1.

The use of TMAH for carrying out anisotropic etching of the substrate 11 is particularly advantageous in combination with the structure of the holed mask 16 described above for leading to the formation of the cavity 20 having the shape illustrated in FIG. 3*c*, in that also this contributes to lateral joining-up of the individual etches.

With reference again to FIGS. 3*a*-3*d*, following TMAH anisotropic etching a chemical vapor deposition (CVD) of tetraethyl orthosilicate (TEOS) is carried out for a thickness of 2 μm, which leads to the formation of a coating layer 22, which is thinner and which coats the side walls and bottom wall of the cavity 20, and of a closing layer 24 which completely closes the openings of the holed mask 16 (FIG. 3*d*).

The closing layer 24 is preferably formed of the same material as the coating layer 22, as part of a continuation of the same step such as CVD of TEOS. Namely, as the TEOS layer is formed on the individual side walls of the mask 17. As the coating layers build up, the deposited material between one mask portion 17 and another mask portion 17 will bridge over, so as to provide a complete block and provide for the formation of a top wall or dielectric diaphragm 26. A suspended structure, such as an inductor or a resistor can then be made, in a way in itself known and not illustrated.

Forming cavities as above described does not entail the deposition of a special sacrificial polycrystalline-silicon layer. Thus, the fabrication process is simpler and more economical due to the reduction in the number of the steps required, and in particular to the elimination of the mask necessary for the definition of the sacrificial polycrystalline-silicon layer.

The process described also enables the fabrication of a cavity 20 having a uniform depth beneath the dielectric diaphragm 26. In contrast, the prior art techniques shown in FIGS. 1*a*-1*c* produce an air gap that is much deeper in the center than on the edges.

Figure 7:
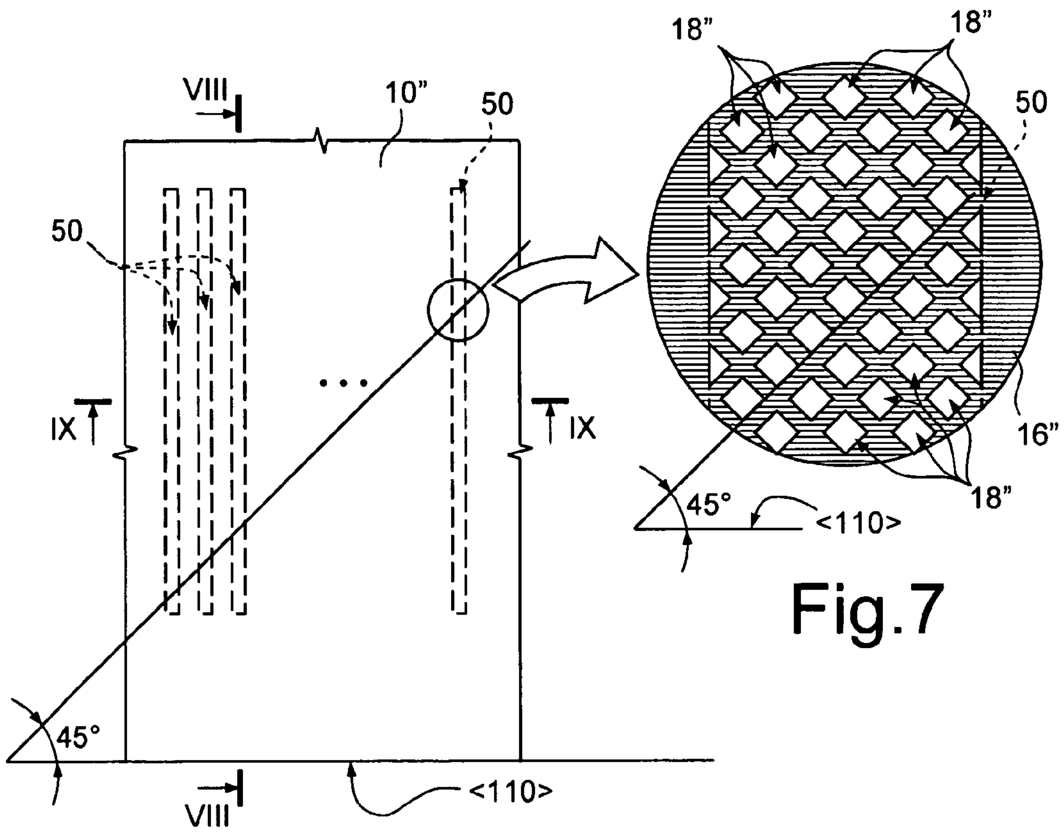
FIG. 7 is a top view of a portion of a semiconductor wafer, in which microfluidic channels have a pre-set orientation with respect to the wafer, at an initial step of a forming process according to one embodiment of the invention.
Figure 8:
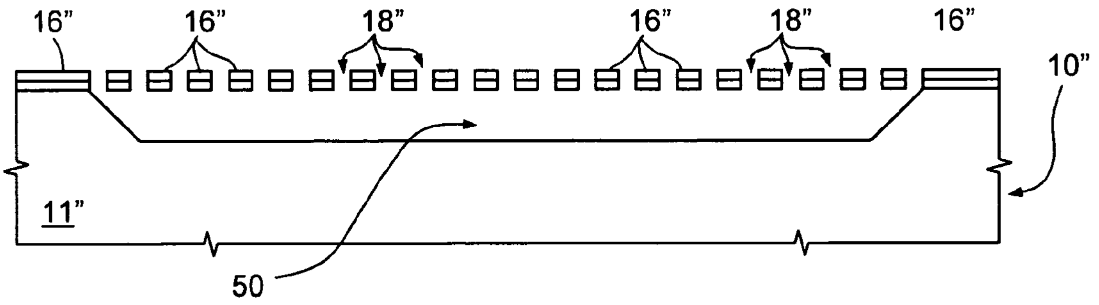
FIG. 8 is a section through the wafer of FIG. 7, taken along the line VIII-VIII of FIG. 7.
Figure 9:
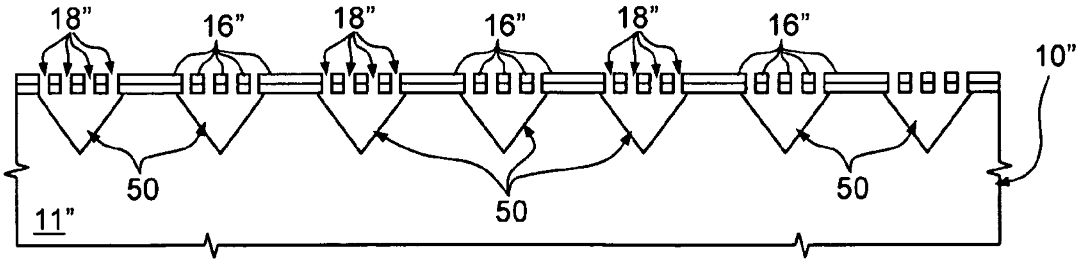
FIGS. 9-12 are sections through the wafer of FIG. 7, taken along the line IX-IX of FIG. 7, in subsequent forming steps according to one embodiment of the invention.

In addition, the present process can be employed for the formation of cavities having, in plan view, any shape whatsoever, and even elongated cavities defining true buried channels, as shown in FIGS. 7 and 9.

The holed mask used in the process could also present a different pattern of the openings. For instance, it is possible to use the pattern shown in FIG. 5, in which the holed mask 16' has openings 18' having a substantially rectangular shape, with the smaller side having a length L1 of, for example, between 1 μm and 3 μm, preferably 2 μm, and the larger side having a length L2 of, for example, between 1 μm and 10 μm, preferably 5-7 μm, and an inclination of 45°±1° with respect to the flat of the wafer 10. The distance between the openings 18' is preferably comparable with that of the smaller side L1, and is hence, for example, between 1 μm and 3 μm.

In addition, the openings 18' are arranged in parallel rows, and the openings 18' belonging to adjacent rows are staggered with respect to one another.

Furthermore, the openings 18' could present a shape slightly different from that illustrated in FIG. 5. In particular, they could present any shape elongated along a prevalent direction having the inclination referred to above with respect to the flat of the wafer 10, for example the shape of a flattened ellipse, a generally quadrangular elongated shape, etc.

The same process can be used to make buried channels connected with the outside world at communication openings, for example elongated channels having two opposite ends and being connected via communication openings set at the ends of the channels themselves. In this case, the openings 18, 18' of the holed mask 16, 16' (see FIG. 4. or FIG. 5) are arranged so as to obtain the desired shape for the cavity 20 or for a plurality of cavities 20. In addition, instead of depositing TEOS after the formation of the cavity 20, polycrystalline silicon is deposited, which forms the coating layer 22 and the closing layer 24.

Figure 6A:
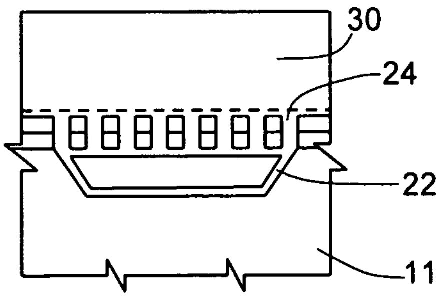
FIGS. 6*a* and 6*b* show cross sections of the wafer of FIG. 3*d* in successive forming steps.
Figure 6B:
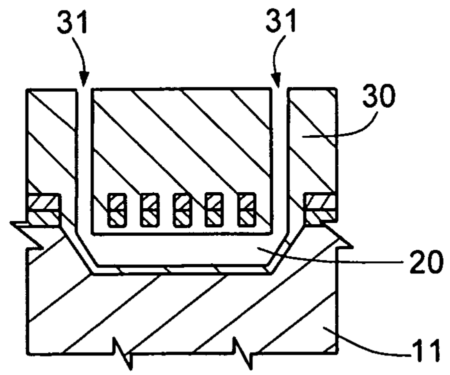

Next, as shown in FIG. 6*a*, an epitaxial layer 30 (not part of this invention) can be grown so as to strengthen the diaphragm 26. Finally, using known etching techniques, the openings 31 are made at the two ends of the cavity or of each cavity 20 (FIG. 6*b*), so as to form areas of access to the cavity or cavities 20. This solution is particularly suited for the fabrication of microreactors for DNA amplification.

A variant of the above described process may be advantageously exploited in manufacturing microfluidic devices including buried channels, such as microreactors for nucleic acid analysis. An example of application of the process to the production of a microreactor will be now described, with reference to FIGS. 7-14.

Initially, a plurality of parallel buried channels 50 (e.g. twelve) are formed in a substrate 11" of a semiconductor wafer 10," wherein nucleic acid amplification reaction, such as PCR (Polymerase Chain Reaction), is to be carried out. The buried channels 50 are first etched using a holed mask 16," having squared apertures 18," sides whereof form an angle of 45°±1° with respect to the flat of the wafer 10." The apertures 18" are moreover arranged such that longitudinal axes A of the buried channels 50 are perpendicular to the flat of the wafer 10." Hence, each buried channel 50 has a trapezoidal longitudinal section (FIG. 8) and a triangular cross section (FIG. 9) when etched to completion. Moreover, all the buried channels 50 have the same length.

Figures 10, 11, 12:
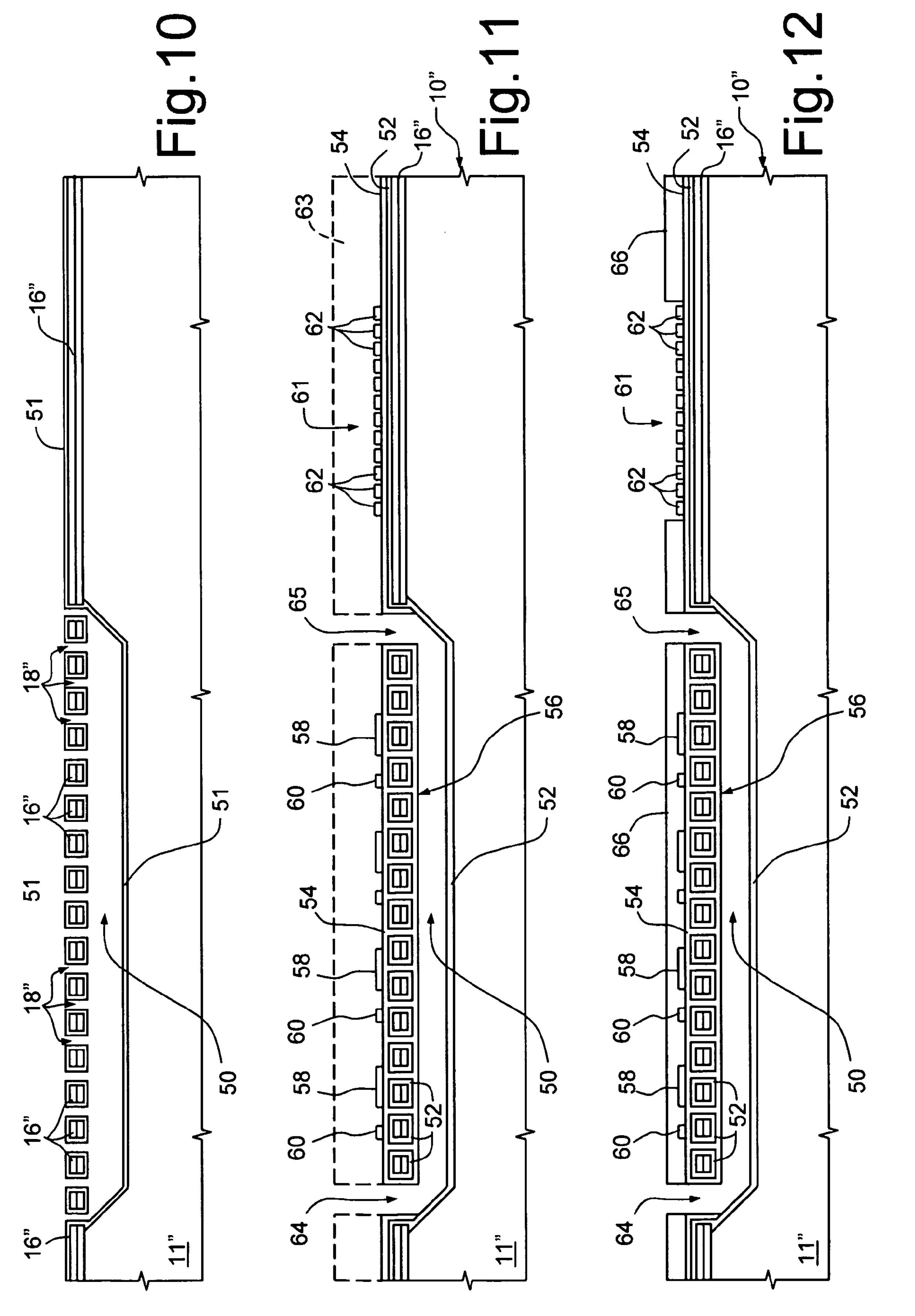

Then, FIG. 10, a polycrystalline silicon is deposited and forms a coating film 51, which covers the walls of the buried channels 50 and only partly occludes the openings 18." Through a thermal oxidation, the coating film 51 is converted into a thermal oxide layer 52, which is thicker and further narrows the apertures 18." For example, the thermal oxide layer 52 has a thickness of 400 nm. In order to completely close the openings 18," TEOS is deposited and forms a closing layer 54, which defines, on top of the buried channels 50, diaphragms 56 (FIG. 11). Thus, the wafer 10" undergoes low thermal stress.

Heaters 58 and temperature sensors 60 are subsequently formed directly on the closing layer 54 and the diaphragms 56, across the buried channels 50. Moreover, an array 61 of electrodes 62 is formed on the closing layer 54, adjacent to longitudinal ends of the buried channels 50.

In one embodiment, the heaters 58, the temperature sensors 60 and the electrodes 62 are made from a metal layer (not shown), e.g. Al, together with connection lines (not shown). In another embodiment (not shown), the heaters 58 are made of polycrystalline silicon. In this case, a polycrystalline silicon layer is first deposited and delineated and connection lines are subsequently formed from a metal layer, together with the electrodes 62.

Diaphragms 56 with a thickness of 2-5 μm, preferably 3 μm, provide sufficient mechanical strength to hold heaters 58 across buried channels 50 having a cross dimension of 200 μm without any substantial risk of failure.

After depositing and photo-lithographically defining a resist layer 63, the diaphragms 56 are etched for opening inlets 64 and outlets 65 at first and second ends of the buried channels 50 (second ends of the buried channels 50 are adjacent to the array 61 of electrodes 62).

Then, a protective layer 66, e.g. of dry resist, is deposited and covers the heaters 58, the temperature sensors 60 and the electrodes 62, as shown in FIG. 12. The protective layer 66 is selectively removed from above the electrodes 62, the inlets 64 and the outlets 65.

Figure 13:
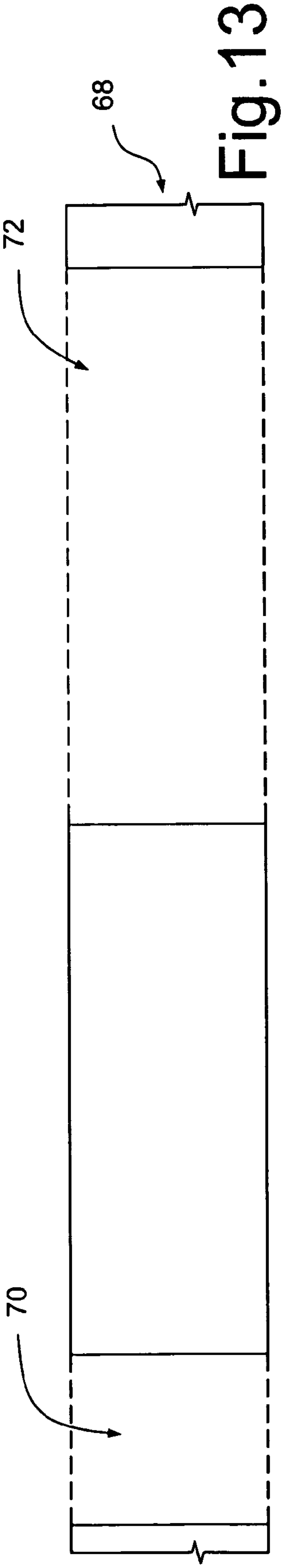
FIG. 13 is cross section through a separate wafer, in a forming step according to one embodiment of the invention.
Figure 14:
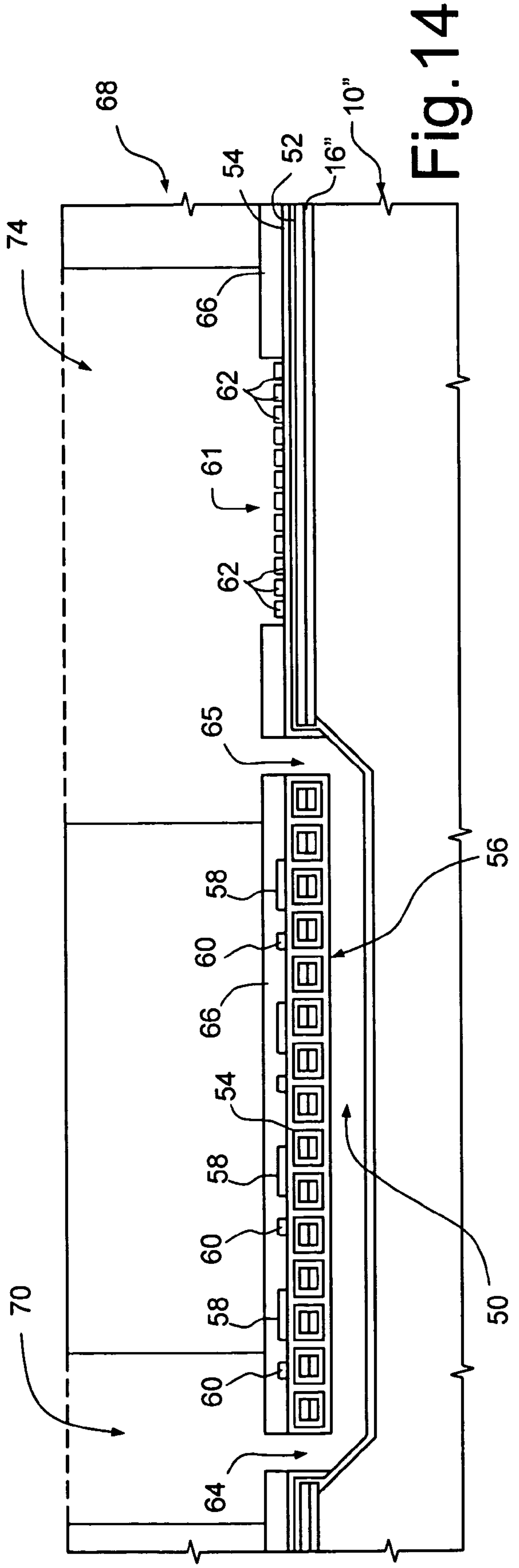
FIG. 14 shows the semiconductor wafer of FIGS. 7-12 and the separate wafer of FIG. 13 bonded together in a final forming step according to one embodiment of the invention.

With reference to FIG. 13, a glass wafer 68 is separately etched to open a through inlet reservoir 70 and a recess 72. The inlet reservoir 70 and the recess 72 are arranged such that, once the glass wafer 68 has been bonded to the semiconductor wafer 10" (namely, on the protective layer 66, FIG. 14), the inlets 64 are accessible from outside through the inlet reservoirs 70 and the outlets 65 communicate to the recess 72. Moreover, the recess 72 defines a detection chamber 74 wherein the array 61 of electrodes 62 is located. The detection chamber 74 is fluidly coupled to the inlet reservoirs 70 via the buried channels 50. The array 61 is to be functionalized before use by grafting DNA probes (not shown) to the electrodes 62.

After sample preparation for extracting DNA from nucleated cells, a biological sample is introduced in the inlet reservoirs 70 and advanced to the buried channels 50 by applying a pressure gradient in a known manner. Once the buried channels 50 have been filled, an amplification reaction (PCR) is carried out by cyclically delivering controlled amounts of thermal energy through the heaters 58. Then, the sample is pushed toward the detection chamber for hybridization of the DNA probes and detection.

Figure 15:
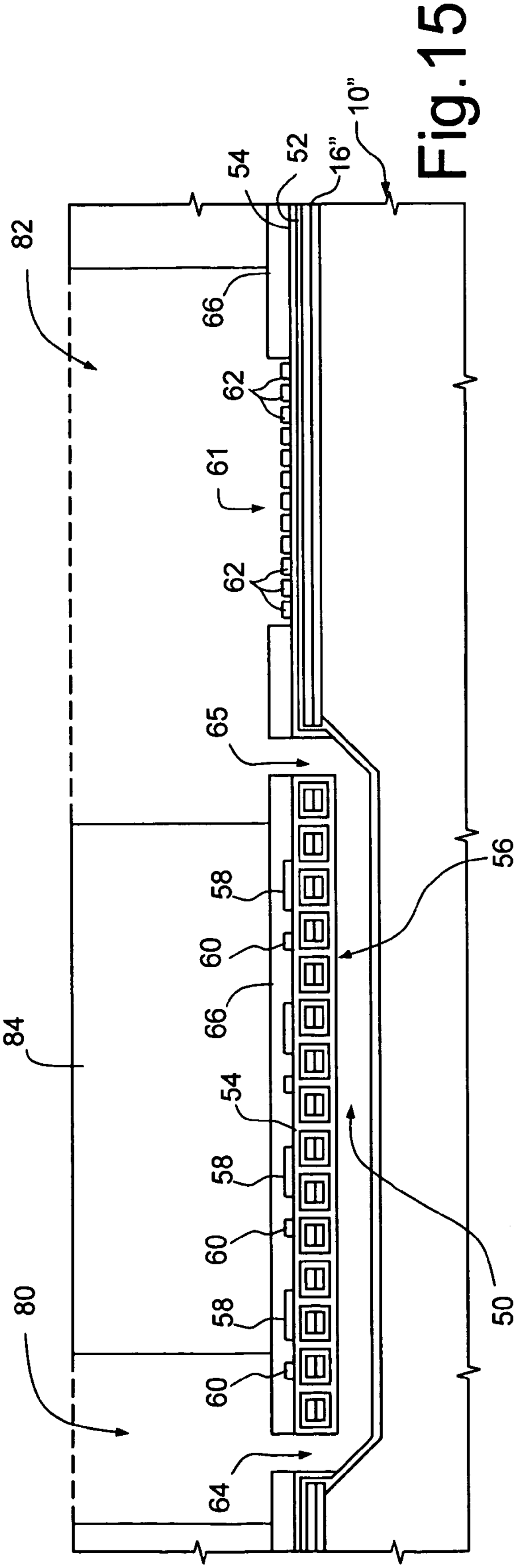
FIG. 15 shows the semiconductor wafer of FIGS. 7-12 in a final forming step according to an alternative embodiment of the invention.

In another embodiment, shown in FIG. 15, an inlet reservoir 80 and a recess defining a detection chamber 82 are formed in a structural layer 84 of a polymeric material, such as resist or SU8, instead of using a separate glass wafer. In this case, the structural layer 84 is deposited on the semiconductor wafer 10" and defined before opening the inlets 64 and the outlets 65.

Forming the heaters 58 and the temperature sensors 60 directly on the closing layer 54 and the diaphragms 56 brings about several advantages.

First, all the process steps may be carried out without almost any alignment problems. In fact, conventional alignment signs on the top surface of the wafer 10" always remain visible, since they are only covered by the holed mask 16." Because of its optical properties, the holed mask 16" does not hide the underlying structures and, in particular, the alignment signs.

In contrast, growing a pseudo-epitaxial layer from a polycrystalline seed layer, in order to strengthen the diaphragms 56, requires some alignment measures to be taken, because polycrystalline silicon hides the alignment signs. Thus, the polycrystalline seed layer and the holed mask 16" should be removed from above the alignment signs, so that a monocrystalline epitaxial layer may be grown thereon directly from the substrate 11." Accordingly, an additional mask for selectively removing polycrystalline seed layer and the holed mask 16" would be required.

Microfluidic motion is improved as well, because biological samples are prevented from directly contacting silicon surface, which is hydrophobic. In contrast, inlet and outlet passages formed through a pseudo-epitaxial polycrystalline layer cannot be passivated by thermal oxidation because the heaters and temperature sensors would be destroyed (either oxidated or melted, depending on the material).

In the second place, opening the inlets 64 and the outlets 65 is simple, because only the diaphragms 56 are to be etched. Moreover, the resist layer 63 may be quite thin, because, although it is thinned during the etch for opening the inlets and the outlets, the etch time is short. For example, the structural layer may have a thickness of 2 μm instead of 7 μm.

Finally, it is clear that numerous modifications and variations can be made to the process described and illustrated herein, without thereby departing from the sphere of protection of one embodiment of the invention, as defined in the attached claims.

For example, the microreactor may comprise one or more of various components such as an injection port, reagent tank, dielectrophoresis cell, capillary electrophoresis channel, chambers or channels for various treatments, micropump, valve, heater, cooler, temperature sensor, detection chamber, detector sensor, power source, controls, display, and the like. In particular, the number and arrangement of these components and their connecting components depends upon the type of treatment to which the specimen fluid is to be subjected. These various components may be integral to the various devices described herein, or may be provided by a mother device on which a disposable microfluidic device is docked. For example, in many preferred embodiments the power source, controls and display are housed on a separate mother device.

The invention claimed is:

1. A process for manufacturing a microfluidic device, comprising the steps of:

forming at least one channel in a semiconductor material body;

forming a dielectric diaphragm above said channel, for closing said channel; and forming heating elements, temperature sensors and an array of electrodes for providing thermal energy inside said channel and control thereof;

wherein said heating elements, temperature sensors and an array of electrodes are formed directly on said dielectric diaphragm.

2. The process according to claim 1, wherein said step of forming at least one channel comprises:

forming a mask on top of said semiconductor material body; and anisotropically etching said semiconductor material body using said mask; and wherein said mask has a plurality of openings, each having a side or a prevalent direction with an inclination of between 44° and 46° with respect to a flat of said semiconductor material body.

3. The process according to claim 2, characterized in that said openings have a side or a prevalent direction with an inclination of 45° with respect to said flat of said semiconductor material body.

4. The process according to claim 2, wherein said step of forming said dielectric diaphragm comprises closing said openings.

5. The process according to claim 4, wherein closing said openings comprises:

depositing a coating film of a semiconductor material, partially occluding said apertures;

thermally oxidizing said coating film, thereby narrowing said openings; and depositing a closing layer of a dielectric material, for completely closing said openings.

6. The process according to claim 5, further comprising the step of depositing a protective layer for covering said heating elements, said temperature sensors and said electrodes.

7. The process according to claim 1, comprising the step of etching said dielectric diaphragm for opening inlets and outlets at opposite ends of said at least one channel.

8. The process according to claim 7, comprising the steps of:

forming an inlet reservoir and a recess in a separate wafer; and bonding said separate wafer to said dielectric diaphragm;

wherein said inlet reservoir and said recess are arranged such that, once said separate wafer has been bonded to said dielectric diaphragm, said inlets are accessible from outside through said inlet reservoir, said outlets communicate to said recess and said electrodes are located in said recess.

9. The process according to claim 7, wherein, before opening said inlets and said outlets, a structural layer of a polymeric material is deposited on said dielectric diaphragm and inlet reservoir and a recess are formed in said structural layer.

10. The process according to claim 2, wherein said anisotropic etching step is carried out using TMAH.

11. A microfluidic device, comprising:

a) at least one channel buried in a semiconductor material body:

b) a dielectric diaphragm above said channel, for closing said channel; and c) heating elements, temperature sensors and an array of electrodes for providing and controlling thermal energy inside said channel, wherein said heating elements, temperature sensors and an array of electrodes are directly formed on said dielectric diaphragm, said array of electrodes being arranged at one end of said channel.

12. The device according to claim 11, comprising a protective layer covering said heating elements, said temperature sensors and said electrodes.

13. The device according to claim 11, comprising inlets and outlets formed through said dielectric diaphragm at opposite ends of said at least one channel.

14. The device according to claim 13, comprising:

a structure formed on said dielectric diaphragm; and an inlet reservoir and a recess formed in said structure, wherein said inlet reservoir and said recess are arranged such that said inlets are accessible from outside through said inlet reservoir, said outlets communicate to said recess and said electrodes are located in said recess.

15. The device according to claim 14, wherein said structure includes a separate wafer bonded on said dielectric diaphragm.

16. The device according to claim 14, wherein said structure includes a structural layer of a polymeric material deposited on said dielectric diaphragm.

17. A method of analyzing a biological sample, comprising applying a biological sample to microfluidic device comprising at least one channel buried in a semiconductor material body, a dielectric diaphragm above said channel for closing said channel, and heating elements, temperature sensors and an array of electrodes for providing thermal energy to said channel and control thereof, wherein said heating elements, temperature sensors and an array of electrodes are arranged directly on said dielectric diaphragm; and analyzing a molecule in said biological sample.

18. The method of claim 17, wherein said molecule in said biological sample is DNA and said analyzing comprises amplification of said DNA to produce amplified DNA and detection of said amplified DNA.

* * * * *